United States Patent [19]

Beard et al.

[11] Patent Number: 5,112,296

[45] Date of Patent: May 12, 1992

[54] BIOFEEDBACK ACTIVATED ORTHOSIS FOR FOOT-DROP REHABILITATION

[75] Inventors: John Beard, Baton Rouge; Verdell M. Banner, Vacherie, both of La.; Mushahid Khan, Houston, Tex.; Norman J. Leonard, Baker, La.

[73] Assignee: The Board of Supervisors of Louisiana State University, Baton Rouge, La.

[21] Appl. No.: 693,816

[22] Filed: Apr. 30, 1991

[51] Int. Cl.$^5$ ............................................. A61F 5/00
[52] U.S. Cl. ........................................ 602/28; 128/905; 128/733; 128/779; 482/4; 482/51; 602/16; 623/53
[58] Field of Search ............... 128/80 E, 80 G, 733, 128/905, 779; 623/24–26, 53, 63–65; 272/70

[56] References Cited

U.S. PATENT DOCUMENTS

| | | |
|---|---|---|
| 1,332,047 | 2/1920 | Lasher . |
| 1,356,327 | 10/1920 | Winiarski . |
| 2,444,839 | 7/1948 | Markkula ........................ 128/80 |
| 3,804,085 | 4/1974 | Eshuls et al. .................... 128/85 |
| 3,805,773 | 4/1974 | Sichau ............................. 128/80 |
| 3,827,430 | 8/1974 | Fadden ............................ 128/80 |
| 3,859,991 | 1/1975 | Theodores ...................... 128/80 |
| 3,986,501 | 10/1976 | Schad ............................. 128/80 |
| 4,005,296 | 1/1977 | Olson ............................. 200/85 |
| 4,289,122 | 9/1981 | Mason et al. ................... 128/80 |
| 4,329,982 | 5/1982 | Heaney .......................... 128/80 |
| 4,492,233 | 1/1985 | Petrofsky et al. .............. 128/905 |
| 4,566,447 | 1/1986 | Dols ............................... 128/80 |
| 4,667,685 | 5/1987 | Fine ............................... 128/905 |
| 4,796,631 | 1/1989 | Grigoryev ...................... 128/80 G |
| 4,817,589 | 4/1989 | Wertz ............................. 128/80 |

*Primary Examiner*—Richard J. Apley
*Assistant Examiner*—Susan L. Weinhoffer
*Attorney, Agent, or Firm*—Robert C. Tucker; William David Kiesel

[57] ABSTRACT

A biofeedback activated orthosis for foot-drop rehabilitation is provided including a lifting mechanism, a control circuit, a muscle activity sensing mechanism, and an electrogoniometer. The lifting mechanism lifts a foot through the swing phase of a gait cycle by way of a drive motor mechanism which pulls a cable passing between a foot brace and a shin brace. The drive motor mechanism allows the cable to unwind upon heel-strike by way of a slip coupling. The drive motor mechanism is controlled by a control circuit which assimilates and processes an incoming electromyographic (EMG) signal from the muscle activity sensing mechanism detected by EMG electrodes placed on the skin above the dorsiflexor muscles of the user. The control circuit also processes a leg position information signal obtained by a radial resistor attached to a knee brace strapped to the knee for sensing the angular position of the lower leg. Activation of the drive motor mechanism will not occur until both processed signals exceed their respective threshold levels set in advance by the user.

20 Claims, 6 Drawing Sheets

BIOFEEDBACK ACTIVATED ORTHOSIS FOR FOOT-DROP REHABILITATION

BACKGROUND OF THE INVENTION

1. Field of the Invention

This invention relates generally to devices used to reduce or eliminate the effect of a condition known as foot-drop, and also to devices used in the rehabilitation of such a condition.

2. Description of the Prior Art

Foot-drop is a neuromuscular disability whereby certain muscles in the leg are incapable of or debilitated in lifting the foot through the swing phase of a person's walking cycle. Such a condition arises in many cases as a result of strokes which damage the electrical paths from the brain to the lower extremities leading to paralysis of the muscles in that region. Persons suffering from multiple sclerosis, traumatic injuries or other diseases involving neuromuscular damage may also experience the troubling effects of this condition.

The motions of the ankle are dorsiflexion (raising the foot) and plantar flexion (lowering the foot), and the motions of the mid-tarsal joint are inversion (turning the foot inward) and eversion (turning the foot outward). When muscles of the ankle and mid-tarsal joints are paralyzed to any extent, the rest of the body must compensate in order to overcome the effects of foot-drop. Because of the independent motion required of these joints, such attempts are rarely effective in alleviating the tendency of the foot and toes to drag as the leg is swung forward during the gait. This invention focuses on the dorsiflexion motion of the ankle, since it is the decreased ability of performing this action that is the most problematic aspect of living with a foot-drop disability.

The muscles in the leg which contribute to the dorsiflexion of the ankle are the tibialis anterior, the extensor digitorum longus, and the extensor hallucis longus. All of these muscles originate at the anterior surface of the fibula, but have separate insertion points. The tibialis anterior inserts on the inner side of the medial cuneiform bone and the base of the first metatarsal. The extensor digitorum longus inserts into the dorsal surfaces of the phalanges of the second and fifth toes, and the extensor hallucis longus inserts at the base of the distal phalanx of the big toe. The strongest muscle of the three, and hence the one most used in dorsiflexion, is the tibialis anterior. For this reason, the operation of a preferred embodiment of the invention will focus on the use of this muscle as the source of biofeedback.

A wide variety of devices have been devised to alleviate the effects of a foot-drop condition. One such apparatus consists of a rigid vertical member formed to cup the calf and heel with a V-shaped strap attached to the shoe. Another device employs a calf collar with a rigid vertical member having a bent and resiliently biased section insertable above the heel of a shoe. A more complicated apparatus use short-leg braces with torsion members coiled about a horizontal pin through the heel of the shoe. Still other devices are as simple as a calf collar with an elastic strap or ligament connected to either the big toe or a clip on the top of the shoe.

Although all of the prior art devices contribute to lifting the foot through the walking cycle, none of these are responsive to the strength remaining in the debilitated muscles. The resultant disadvantage, therefore, is that the affected muscles are not used when the device is worn, and atrophy and further degeneration of these muscles is the inevitable consequence. Likewise, in those devices which do not exercise the leg in plantar flexion, a similar effect will be seen in those muscles. This invention succeeds in overcoming these disadvantages by relying on the person's own residual muscle activity in the form of electrical biofeedback to operate the invention. This method and apparatus will thereby increase the chances of permanently alleviating foot-drop by rehabilitating the dorsiflexor muscles over time simply through using the device to assist in walking.

Figure 9:
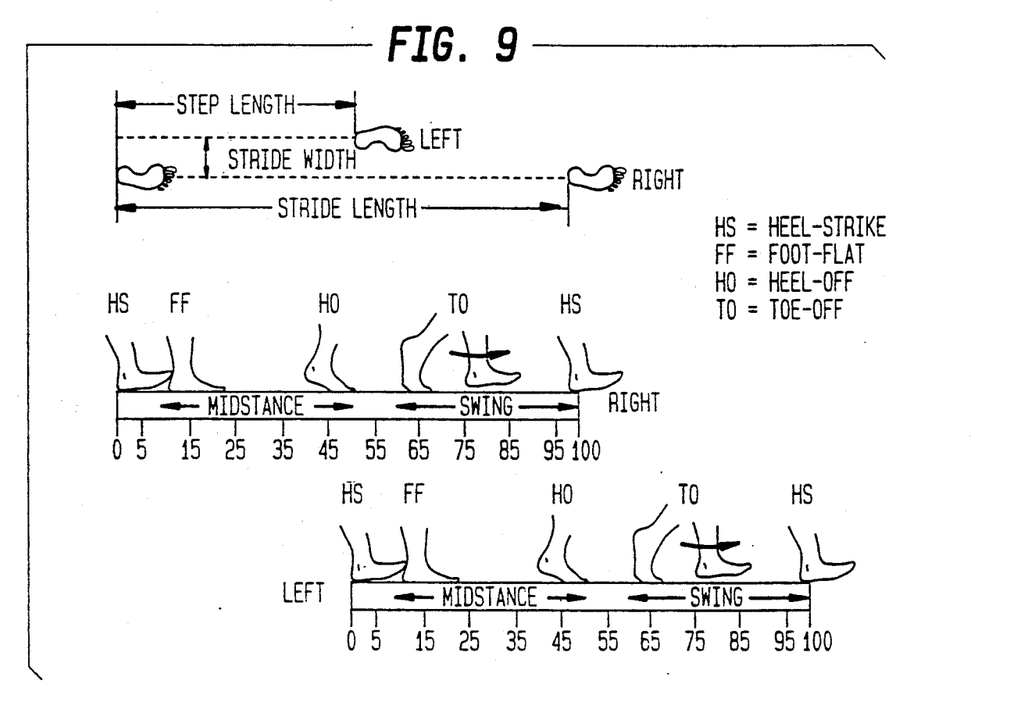
FIG. 9 is a diagram showing the phases of a gait cycle for left and right legs, illustrating the dynamics of foot contact with a walking surface.

In order to fully understand the functioning of the invention, a brief explanation of the biomechanics of the leg and the phases of the human gait cycle is necessary. Normal walking consists of two major phases: the stance phase and the swing phase. As can be seen from FIG. 9, The stance phase occupies 60% of a single gait cycle beginning with the strike of the heel on the ground (heel-strike) and concluding with the toes leaving the ground (toe-off). Subphases of the stance are, respectively, heel-strike, foot-flat, heel-off and toe-off. The remaining 40% of the gait is between toe-off and heel-strike and is referred to as the swing phase. It is during this phase that it becomes necessary for the foot to be pulled upward so that a proper heel-strike can be made at the conclusion of the swing phase. Because foot-drop prevents such a responsive motion, this invention is provided which will overcome this effect by becoming mechanically active during the swing phase of the gait cycle. Precise timing is critical to accomplishing this task, and a logical solution to the problem is to use whatever residual activity exists in the debilitated muscles that control such motion to trigger the mechanical function of the invention. Electromyographic activity and biofeedback provide such a solution, and a brief explanation of this process follows.

Detectable muscle activity stems from chemical reactions taking place within the muscles during contraction. The muscle fibers are encased in membranes which are polarized due to these reactions, and are electrically positive on the outside with respect to the interior of the fiber. The membrane undergoes depolarization immediately prior to contraction so that this area becomes electrically negative with respect to the remainder of the muscle. The effects of this process are evidenced by a voltage existing between two electrodes placed on the skin above the subject muscle. Such a voltage is commonly referred to as electromyographic (EMG) activity or EMG voltage.

Periods of muscle activity are always followed by rest in order to minimize the expenditure of energy. Muscle activity is highest at the beginning of the stance phase and decreases through mid-stance. In late-stance, however, activity increases in preparation for the swing phase where the dorsiflexors lift the foot to clear the ground. When the heel strikes the ground at the end of the swing, considerable angular momentum is developed and a sharp muscle contraction is required to decelerate the foot. The relationship, therefore, between the level of EMG activity and the location of the foot throughout the gait cycle is predictable and is used in this invention as one of the two criteria for operating the orthosis. As explained herein, the other criterion for activation of the orthosis is based on the position of the leg during the gait cycle as detected by a simple potentiometer. Satisfaction of both of these criteria results in activation of the orthosis in an embodiment of the invention, and a rehabilitative effect should be seen over time as the user strengthens the dorsiflexor muscles used in the biofeedback process.

SUMMARY OF THE INVENTION

It is, therefore, an object of this invention to provide a biofeedback activated orthosis and method which alleviate the effects of foot-drop.

It is also an object of this invention to provide a biofeedback activated orthosis and method which will assist in the rehabilitation of a foot-drop condition as the orthosis is used over a period of time.

A further object of this invention is to provide a biofeedback activated orthosis whose operation is a function of the residual electromyographic activity of the affected muscles.

Yet another object of this invention is to provide a biofeedback activated orthosis which can be used in a therapeutic or rehabilitative environment by allowing for control of the input by the user depending on the user's strength and mobility.

Accordingly, a biofeedback activated orthosis is provided including a lifting means which is used to lift a foot through the swing phase of a gait cycle. The lifting means includes a drive means which pulls a cable passing between a foot brace and a shin brace and allows the cable to unwind upon heel-strike by way of a slip coupling. The lifting means is controlled by a control means which assimilates and processes an incoming EMG signal detected by a muscle activity sensing means placed on the skin above the dorsiflexor muscles. The control means also processes a leg position information signal obtained by the use of an electrogoniometer means attached near the knee for sensing the correct angular position of the leg. Activation of the lifting means will not occur until both processed signals exceed their respective threshold levels set in advance by the user or a clinician.

DETAILED DESCRIPTION OF THE PREFERRED EMBODIMENTS

Figure 1:
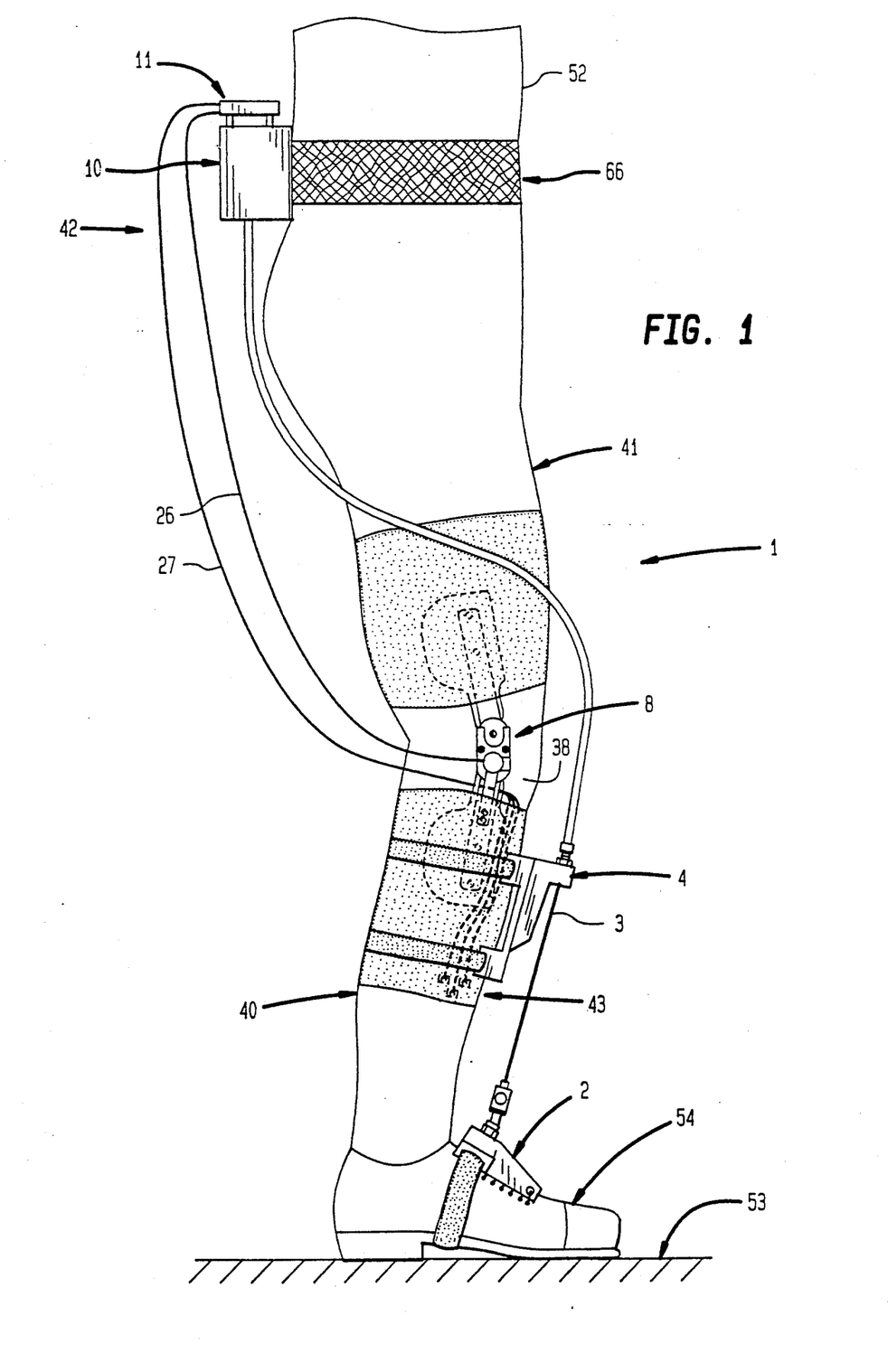
FIG. 1 is a side view of an embodiment of the invention in an operating configuration.

Referring more particularly to the drawings, FIG. 1 is an overall view of a preferred embodiment of a biofeedback-activated orthosis 1 for foot-drop rehabilitation in an operating configuration on a user 52. The main assemblies of the orthosis 1 are the lifting means 42, the control means 11, the muscle activity sensing means 43, and the electrogoniometer means 8. The muscle activity sensing means 43 detects the electromyographic voltage potential from the surface of the skin 38 and sends it to the control means 11 for further processing. The electrogoniometer means 8 supplies an additional criterion for activation of the orthosis 1 by detecting the angular position of the lower leg 40 during a gait cycle. The control means 11 accepts the raw EMG data from the muscle activity sensing means 43 and the leg position information from the electrogoniometer means 8 and provides the lifting means 42 with a processed electrical signal at the precise time that the foot 54 should be lifted from the ground 53. The lifting means 42 then applies the force necessary to lift the foot 54 during the swing phase of the walking cycle.

In a preferred embodiment, the lifting means 42 comprises a foot brace 2, a shin brace 4, a drive means 10 for lifting the foot 54, a carrying means 66 for supporting the drive means 10, and a cable 3 connected on one end to the foot brace 2 and on the other end to the drive means 10, and passing through the shin brace 4.

Figure 2:
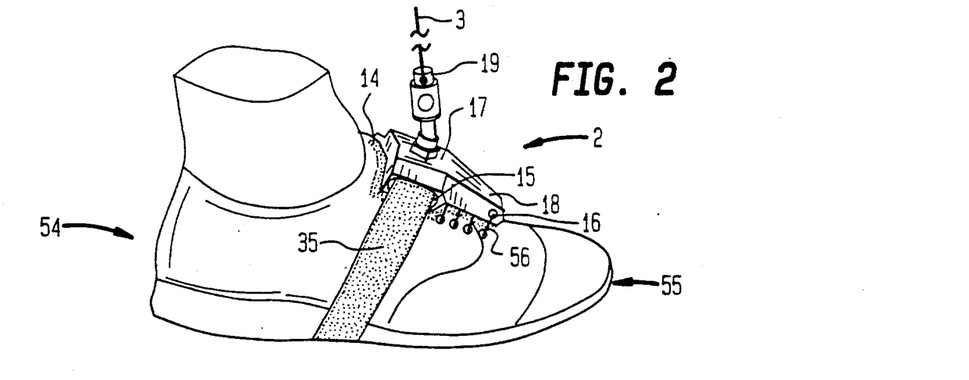
FIG. 2 is an isometric view of the foot brace, cable and cable swivel connection of an embodiment of the invention.

Foot brace 2, shown in more detail in FIG. 2, is secured to the foot 54 of the user 52 by foot brace straps 35 which pass through two foot brace strap slots 15 on either side of foot brace 2 and wrapped around the front portion 55 of the foot 54, and includes a lace hole 16 formed horizontally through the frontal section 18 of the foot brace 2 for securing the foot brace 2 to the shoe laces 56. For comfort in wearing the foot brace 2, a foot brace cushion 14 is adhesively attached to the underside of the foot brace 2. A cable swivel connection 19 is located on the dorsal section 17 of the foot brace 2 in order to accommodate a cable 3 for lifting the foot 54 through a gait cycle.

Figure 3:
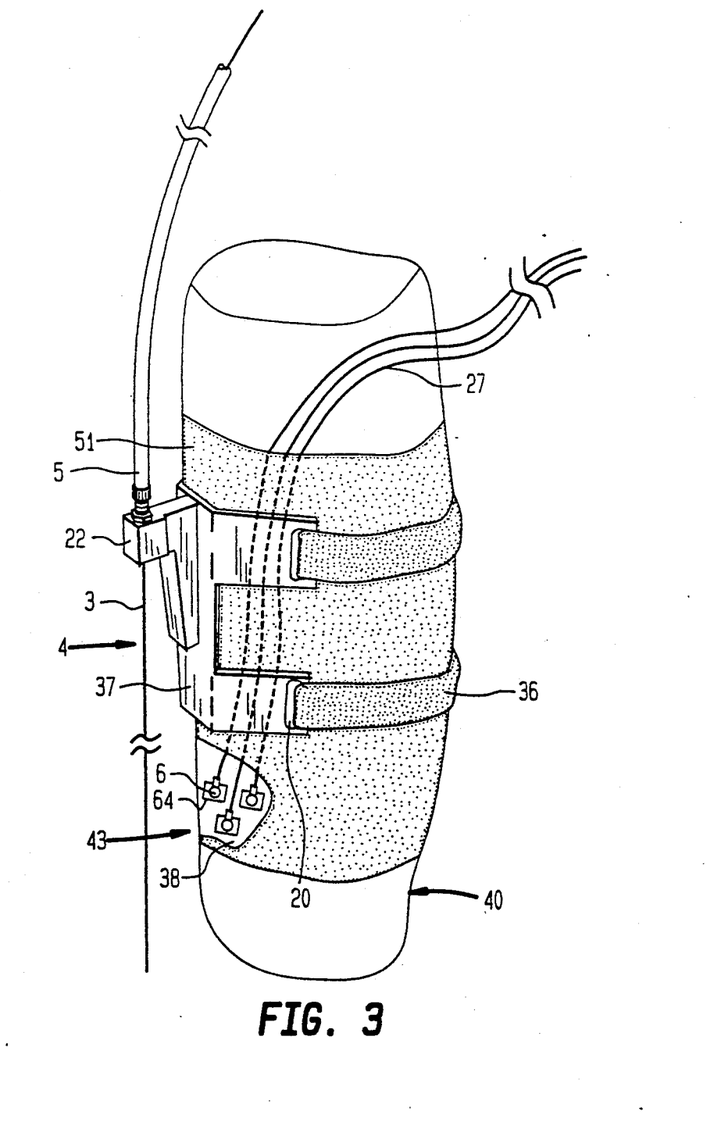
FIG. 3 is an isometric view of the shin brace and cable housing connection of an embodiment of the invention.

In FIG. 3, a shin brace 4 is shown secured to the lower leg 40 of the user 52. The shin brace 4 has a set of four shin brace strap slots 20, two slots on either side, through which are passed shin brace straps 36 for keeping the shin brace body 37 pressed against an elastic leg wrap 51 around the lower leg 40 during operation. Support arm 22 is formed onto the front of the shin brace body 37 for keeping the cable 3 away from the lower leg 40 and providing support for cable housing 5, which is attached to the support arm 22. Below the shin brace 4, the muscle activity sensing means 43 comprises three electromyographic (EMG) electrodes 6 which are attached to surface sensors 64 on the skin 38 above the anterior tibialis muscle. EMG wires 27 connect to the EMG electrodes 6 and lead away from the lower leg 40 to the control means 11.

Figure 4:
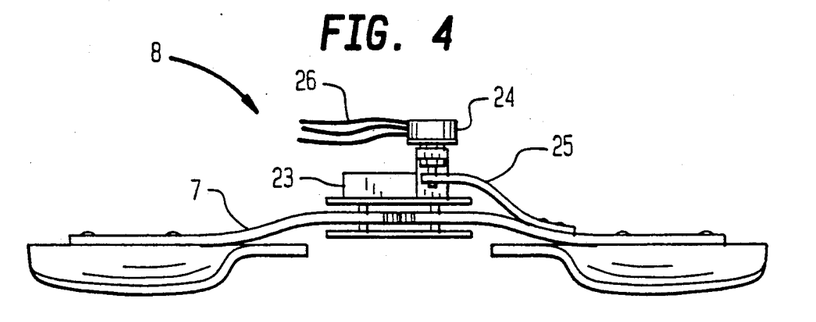
FIG. 4 is a rear view of the knee brace and the electrogoniometer of an embodiment of the invention.
Figure 5:
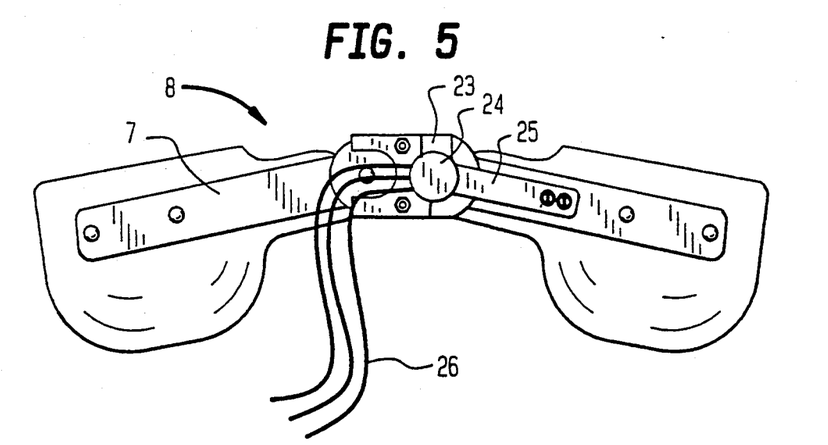
FIG. 5 is a side view of the knee brace and the electrogoniometer of an embodiment of the invention.

FIGS. 4 and 5 more clearly depict the electrogoniometer means 8, comprising a knee brace 7, common in the field of physical therapy, a radial resistor 24, a resistor bracket 23 and a resistor arm 25. Radial resistor 24 is operated by movement of resistor arm 25 attached to knee brace 7, and the resulting electrical signal is carried to the control means 11 by way of resistor wires 26 connected to the radial resistor 24. The signal sent to control means 11 represents the angular relationship between the lower leg 40 and the thigh 41, and is used as an additional criterion for operation of the orthosis 1 as further explained herein.

Figure 6:
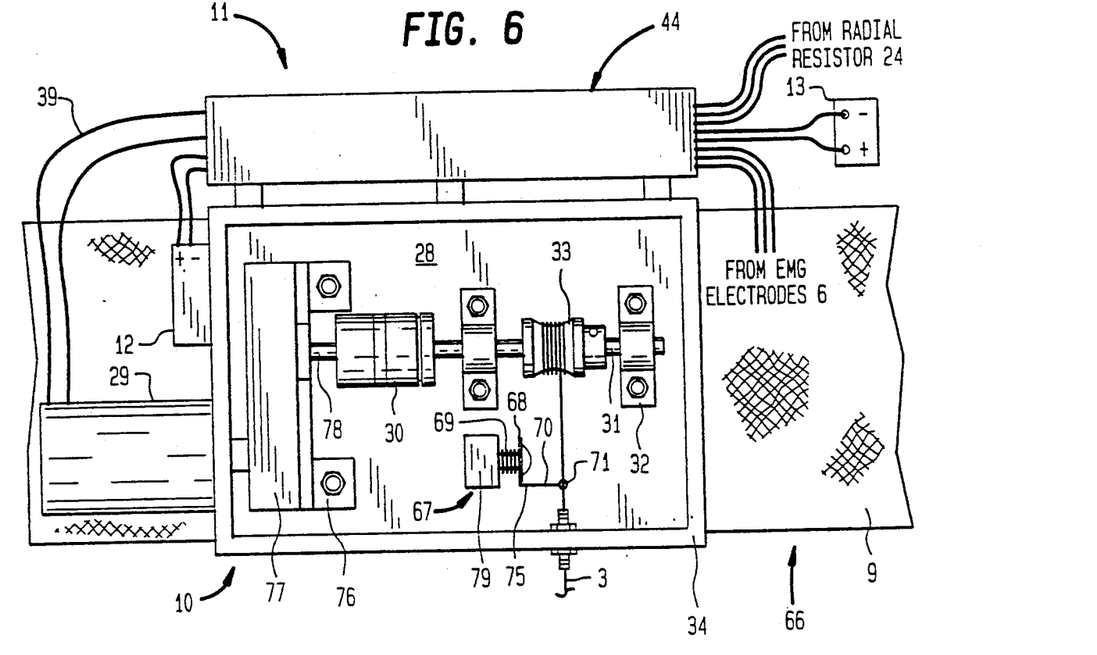
FIG. 6 is a front view of the drive means and control means of an embodiment of the invention with the necessary electrical connections.

Drive means 10 and control means 11 are shown in FIG. 6. Control means 11 is physically secured to drive means 10 by any means which does not interfere with the operation of the electronics and includes a control circuit 44, a first power supply 12, and a second power supply 13. First power supply 12, preferably a 9-volt DC dry cell battery, provides an operating current to both the control circuit 44 and the radial resistor 24. Second power supply 13, preferably a 12-volt DC wet cell battery, provides the operating current to gear motor 29 after being passed through control circuit 44, which is electrically connected to gear motor 29 by way of gear motor wires 39. Drive means 10 preferably comprises a baseplate 28 having a motor brace 76 which in turn supports the gear box portion 77 of gear motor 29. In a preferred embodiment, gear motor 29 should have a gear ratio of about 100:1 and be operable by a 12-volt power supply. Baseplate 28 also supports two Teflon bearings 32 and is attached to carrying means 66. One embodiment of carrying means 66 could be a waist strap 9 worn by user 52. A drive shaft 31 is supported between bearings 32 and carries a spool 33 for winding the cable 3 as drive means 10 is operated. A slip coupling means 30, preferably having a maximum torque rating of about 10 inch-pounds, is attached between the mating ends of drive shaft 31 and motor shaft 78 of gear motor 29 to allow the user 52 to unwind cable 3 as the foot 54 makes heel-strike with the ground 53 at the end of the swing phase of the gait. In a preferred embodiment, the mechanical components of drive means 10 may be encased within a housing 34 secured to baseplate 28 to protect gear motor 29, drive shaft 31, and motor shaft 78 from entangling the clothing of the user 52. A backlash inhibiting means 67 prevents backlash of cable 3 by maintaining a minimum amount of tension in cable 3 at all times. In a preferred embodiment, backlash inhibiting means 67 is a screw 68 placed into a protruding portion 79 of baseplate 28 with a coil spring 69 wound about it and fixed at its base to baseplate 28. A spring washer 75 is used to retain the body of coil spring 69 on screw 68. Spring arm 70 of coil spring 69 extends from screw 68 to cable 3 and contains a spring loop 71 through which cable 3 remains in slidable communication.

Figure 7:
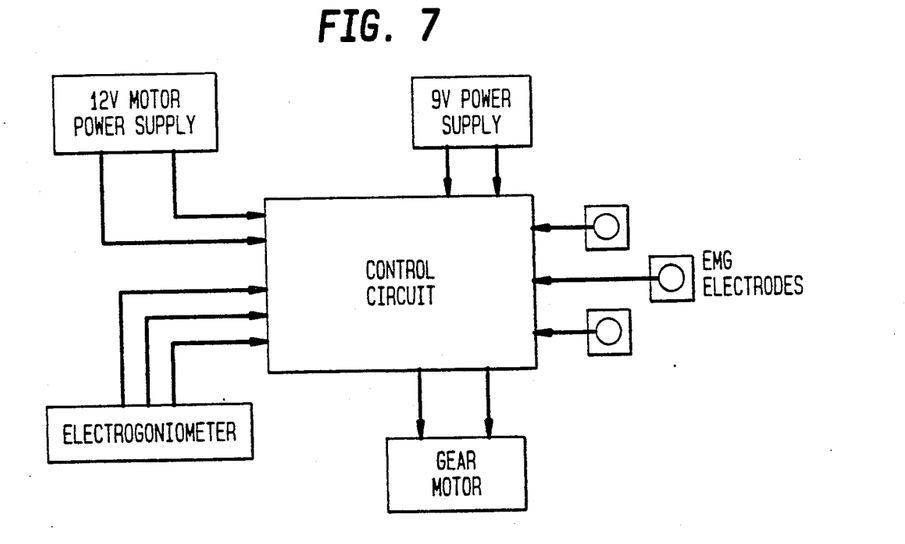
FIG. 7 is a schematic diagram showing the electrical connections required for operation of an embodiment of the invention.

A schematic diagram of the electrical connections necessary for proper operation of the orthosis 1 is shown in FIG. 7. With the exception of gear motor 29, all electrical components feed into control circuit 44. If both the criteria of muscle activity from the EMG electrodes 6 and the leg position from radial resistor 24 are simultaneously satisfied, a processed signal is sent to activate gear motor 29 for timely applying tension to the cable 3, thereby pulling upward on foot brace 2. If either of these two criteria become unsatisfied at any time, gear motor 29 will become deactivated.

Figure 8:
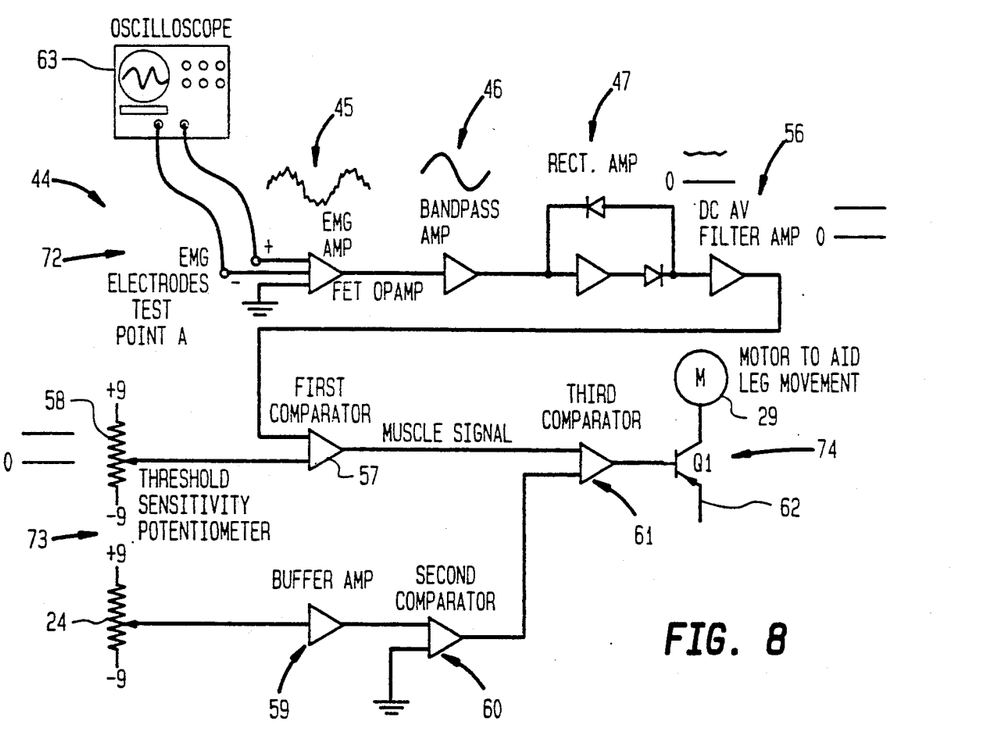
FIG. 8 is a schematic diagram of the control means depicting the major electronic components involved in processing the EMG signal and the electrogoniometer input.

A detailed schematic of the electronics in control circuit 44 is shown in FIG. 8. Control circuit 44 is composed of three main parts: EMG signal processing means 72, electrogoniometer processing means 73, and activation means 74. In the EMG signal processing means 72, a high impedance, high gain differential amplifying means 45 accepts the raw EMG input signal in AC form from the positive and negative terminals of EMG electrodes 6 and amplifies it while suppressing extraneous signal aberrations that may be attributable to other muscle activity or movement of the EMG wires 27. The amplified signal proceeds to a band pass filtering means 46 where unwanted lower and higher frequency signals attributable to motion of the EMG electrodes 6, nearby muscles, and other electrical sources are filtered out according to a predetermined range of signal frequencies to be used in activating gear motor 29. Rectifying means 47 then receives the EMG signal and reverses all negative portions in order to create a uniformly positive DC output. This rectified signal is passed through a DC averaging means 56 which creates a constant signal level. First comparator means 57 compares this signal to a threshold level set in advance by the adjustment of a threshold sensitivity potentiometer 58 on control circuit 44. If the processed signal exceeds the preset threshold, the signal is allowed to proceed to the next stage of the processing.

Radial resistor 24 also sends a current to control circuit 44, where a buffer amplifier 59 in the electrogoniometer processing means 73 buffers the signal and prevents loading the rest of the control circuit 44 before it enters a second comparator means 60. Second comparator means 60 compares this signal to a preset level of voltage associated with the optimum angular position of the lower leg 40. If this level is exceeded by the output from radial resistor 24, the signal is advanced to a third comparator means 61 within the activation means 74 where both the leg position information signal and the processed EMG signal are added and compared to determine whether both criteria for activation of the gear motor 29 are met. If both conditions are satisfied simultaneously, the resultant signal biases a transistor 62 which allows activation of gear motor 29 by current flow from the second power supply 13. Gear motor 29 will remain activated until either the leg position information signal or the processed EMG signal fall below their respective preset threshold levels.

Figure 10:
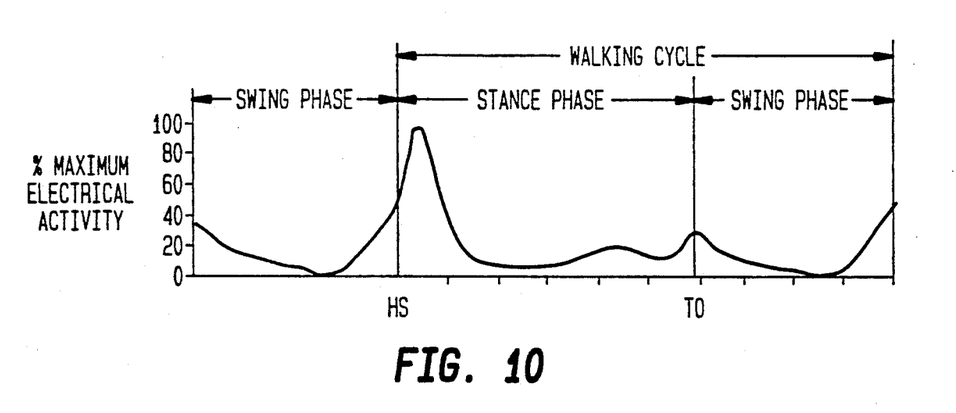
FIG. 10 is a graph which shows a typical relationship between the level of EMG activity and the phases of a gait cycle.

The basis for determining the appropriate threshold levels for either of these inputs is a clinical decision as to the muscle strength and mobility of the user 52 prior to therapy. Such a determination may be made in part from an experimentally obtained relationship between the phases of the user's walking cycle and the level of raw EMG activity produced during those phases. A typical graph of this relationship is shown in FIG. 10. Primary sources of electrical adjustment of the orthosis 1 are fine tuning of the threshold sensitivity potentiometer 58 and the radial resistor 24. Adjustments to the variable gain on the differential amplifier 45, modifications of the band pass filter 46, and other esoteric electrical alterations may also be made to the control circuit 44 by someone skilled in the electronic arts in order to achieve the needs of particular user 52.

In operation, the area to be used for the EMG electrodes 6 is shaved to provide a smooth surface on the skin 38. The three EMG electrodes 6 represent positive, negative and ground leads and are preferably placed in a triangular configuration on the skin 38 above the dorsiflexor muscle to be used, usually the tibialis anterior, using disposable surface sensors 64 and conductive gel common in the art. An oscilloscope 63 is used to test the appearance of the raw EMG signal at the point on the control circuit 44 just before the signal enters the differential amplifier 45. This is shown as Test Point A in FIG. 8. If the electrodes 6 are improperly placed on the skin 38, a 60-Hz signal will appear due to lighting or other electrical sources. Electrodes 6 should be firmly placed so that the oscilloscope signal appears as close to a straight line as possible when the muscles of the lower leg 40 are completely relaxed. To test whether or not the waveform is sufficient in strength to activate the drive means 10, the knee brace 7 must be bent so that an increasingly higher signal is sent from radial resistor 24. If the EMG threshold level is set low, and gear motor 29 activates while the muscles are still in relaxation, the electrodes 6 should be adjusted to minimize the effects of lighting and other 60-Hz power sources, and to prevent the gear motor 29 from activating merely when the radial resistor 24 reaches its preset threshold level. When the electrodes 6 are properly attached, the dorsiflexor muscles should be contracted to create a signal at Test Point A which will give the clinician a basis for setting the threshold sensitivity potentiometer 58. Once this level is set and then exceeded by the signal from the muscular contraction, and the unattached knee brace 7 is bent to a position corresponding to the threshold level of the radial resistor 24, gear motor 29 should activate.

By way of example, if an EMG level of 0.4 microvolts is indicated on the oscilloscope 63 when the muscles in the affected lower leg 40 are relaxed, and this level increases to 11.0 microvolts in full contraction, a possible setting for the threshold sensitivity potentiometer 58 would be 8.0 microvolts. At this setting, the user 52 would be able to exceed the threshold level without undue effort, but would still be required to exert enough muscular energy to facilitate a rehabilitative effect.

Knee brace 7 is placed on the outside of the thigh 41 and lower leg 40, and elastic leg wraps 51 are then carefully placed above and below radial resistor 24 to secure knee brace 7 to the user 52. Foot brace 2 and shin brace 4 are then strapped to the lower leg 40 such that support arm 22 on shin brace 4 is directly over the dorsal section 17 of the foot brace 2 and cable swivel connection 19. The waist strap 9 and attached drive means 10 are then worn by the user 52, and the cable 3 is passed through support arm 22 on shin brace 4 and down to the foot brace 2. When the cable housing 5 is secured, the cable 3 is pulled tight and attached to the cable swivel connection 19 on the foot brace 2. When all mechanical and electrical connections have been made, the EMG signal is rechecked to verify that the electrodes 6 have not been disturbed. The user 52 is then directed to begin a walking cycle to test the torque necessary to allow slippage of the slip coupling means 30. The proper torque is achieved through trial and error, but should be low enough to allow foot-flat through slippage of the slip coupling means 30 immediately after heel-strike, but high enough to prevent slippage during winding of the cable 3 at the start of the swing phase.

Although the present invention has been described in detail with reference only to the presently-preferred embodiment, it will be appreciated by those of ordinary skill in the art that various modifications can be made without departing from the invention. Accordingly, the invention is limited only by the scope and spirit of the following claims.

We claim:

1. A biofeedback activated orthosis for foot-drop rehabilitation, comprising:
   a. a lifting means for mechanically lifting a foot during the swing phase of a walking cycle, attachable to a human body at a point above said foot and attachable to said foot;
   b. a muscle activity sensing means for detecting muscle activity and transmitting data relating to said activity to a control means, attached to an affected leg of said human body and operatively connected to said control means;
   c. a control means for receiving and processing said data from said muscle activity sensing means and controlling operation of said lifting means, operatively connected to said lifting means and said muscle activity sensing means; and
   d. an electrogoniometer means for detecting the angular position between the thigh and the shin of said leg, and for transmitting data reflecting said position to said control means, operatively connected to said leg of said human body and said control means.

2. An orthosis according to claim 1, wherein said electrogoniometer mean includes:
   i. a radial resistor for detecting a change in electrical resistance as said angular position varies during said gait;
   ii. a knee brace operatively attached to the knee of said leg for holding said radial resistor and further comprising a resistor arm attached to said radial resistor for varying the output of said radial resistor when measuring said angular position; and
   iii. a plurality of wires, each said wire electrically connected at one end to said radial resistor and electrically connected at the other end to said control means for transmitting said change in electrical resistance to said control means.

3. An orthosis according to claim 1, wherein said lifting means comprises:
   i. a foot brace attachable to said foot;
   ii. a cable operatively attached at one end to said foot brace and at the other end to a drive means;
   iii. a shin brace attachable to the shin of said affected leg and including a support arm;
   iv. a drive means for applying tension to said cable in lifting said foot brace, operatively connected to said other end of said cable;
   v. a cable housing in which said cable is contained attachable at one end to said support arm and attachable at the other end to said drive means; and
   vi. a carrying means worn on said human body for carrying said drive means and said control means.

4. An orthosis according to claim 3, wherein said carrying means is a waist strap or belt.

5. An orthosis according to claim 4, wherein said drive means includes:
   a. a gear motor electrically connected to said control means;
   b. a baseplate attachable to said carrying means;
   c. a slip coupling means attached to the motor shaft of said gear motor for allowing said cable to unwind upon heel-strike of said foot;
   d. a drive shaft attached to the opposite side of said slip coupling means for transmitting said torque produced by said gear motor; and
   e. a plurality of bearings for supporting said drive shaft fixedly attached to said baseplate and for providing rotatable communication with said drive shaft.

6. An orthosis according to claim 5, further comprising a spool having a concave rotating surface attached to said drive shaft for collecting and releasing said cable as said foot is lifted and allowed to drop upon heel-strike, respectively.

7. An orthosis according to claim 6, wherein said drive means further includes:

f. a backlash inhibiting means attachable to said baseplate and said cable for preventing entanglement of and maintaining tension upon said cable at all times.

8. An orthosis according to claim 7, wherein said backlash inhibiting means includes:
   i) a shaft fixedly attached on one end to said baseplate, said shaft further comprising a spring stop plate attached at the opposite end of and perpendicular to said shaft; and
   ii) a coil spring wound about said shaft having one end fixedly retained relative to said baseplate and an opposite end including a spring arm slidably engaged with and resiliently biased against said cable for maintaining tension in said cable.

9. An orthosis according to claim 5, wherein said drive means further includes:
   f. a backlash inhibiting means attachable to said baseplate and said cable for preventing entanglement of and maintaining tension upon said cable at all times.

10. An orthosis according to claim 9, wherein said backlash inhibiting means includes:
    i) a shaft fixedly attached on one end to said baseplate, said shaft further comprising a spring stop plate attached at the opposite end of and perpendicular to said shaft; and
    ii) a coil spring wound about said shaft having one end fixedly retained relative to said baseplate and an opposite end including a spring arm slidably engaged with and resiliently biased against said cable for maintaining tension in said cable.

11. An orthosis according to claim 3, wherein said drive means includes:
    a. a gear motor electrically connected to said control means;
    b. a baseplate attachable to said carrying means;
    c. a slip coupling means attached to the motor shaft of said gear motor for allowing said cable to unwind upon heel-strike of said foot;
    d. a drive shaft attached to the opposite side of said slip coupling means for transmitting said torque produced by said gear motor; and
    e. a plurality of bearings for supporting said drive shaft fixedly attached to said baseplate and for providing rotatable communication with said drive shaft.

12. An orthosis according to claim 11, further comprising a spool having a concave rotating surface attached to said drive shaft for collecting and releasing said cable as said foot is lifted and allowed to drop upon heel-strike, respectively.

13. An orthosis according to claim 12, wherein said drive means further includes:
    f. a backlash inhibiting means attachable to said baseplate and said cable for preventing entanglement of and maintaining tension upon said cable at all times.

14. An orthosis according to claim 13, wherein said backlash inhibiting means includes:
    i) a shaft fixedly attached on one end to said baseplate, said shaft further comprising a spring stop plate attached at the opposite end of and perpendicular to said shaft; and
    ii) a coil spring wound about said shaft having one end fixedly retained relative to said baseplate and an opposite end including a spring arm slidably engaged with and resiliently biased against said cable for maintaining tension in said cable.

15. An orthosis according to claim 5, wherein said drive means further includes:
    f. a backlash inhibiting means attachable to said baseplate and said cable for preventing entanglement of and maintaining tension upon said cable at all times.

16. An orthosis according to claim 15, wherein said backlash inhibiting means includes:
    i) a shaft fixedly attached on one end to said baseplate, said shaft further comprising a spring stop plate attached at the opposite end of and perpendicular to said shaft; and
    ii) a coil spring wound about said shaft having one end fixedly retained relative to said baseplate and an opposite end including a spring arm slidably engaged with and resiliently biased against said cable for maintaining tension in said cable.

17. An orthosis according to claim 1, wherein said control means includes:
    i) a control circuit electrically connected to said lifting means for processing a raw electromyographic signal, for receiving a positional information signal from said electrogoniometer means, and for comparing said signals to preset threshold levels to determine whether said lifting means is to be activated;
    ii a first power supply electrically connected to said control circuit for supplying operating power to said control circuit and to said electrogoniometer means; and
    iii. a second power supply electrically connected to said control circuit for supplying operating power to said lifting means.

18. An orthosis according to claim 17, wherein said control circuit includes:
    i. an EMG signal processing means electronically connected to said muscle activity sensing means for establishing a constant DC signal level from said raw EMG signal and for comparing said DC signal to a preset EMG threshold level for further processing, further comprising:
       a. an amplifying means for amplifying said raw EMG signal received by said muscle activity sensing means;
       b. a filtering means electronically connected to said amplifying means for discarding frequencies of said raw electromyographic signal attributable to non-muscular sources and for transferring frequencies of said signal specific to said muscle activity;
       c. a rectifying means electronically connected to said filtering means for creating a rectified signal from said amplified signal;
       d. an averaging means electronically connected to said rectifying means for creating a constant DC signal from said rectified signal;
       e. a first comparator means electronically connected to said averaging means for comparing said constant DC signal to a first threshold level, and for allowing said signal to continue through said control circuit if said signal level exceeds said first threshold level;
    ii. an electrogoniometer processing means electronically connected to said EMG signal processing means for comparing said positional information signal to a preset positional threshold level for further processing, further comprising:
       a. a buffer amplifying means for buffering said positional information signal received from said electrogoniometer means;

b. a second comparator means for comparing said buffered positional information signal to a second threshold level and for allowing said signal to continue through said control circuit if said signal exceeds said second threshold level;

iii. an activation means electronically connected to said EMG signal processing means and to said electrogoniometer processing means for determining whether said threshold levels of said respective means are exceeded simultaneously, and for activating said lifting means if such a condition is satisfied, further comprising:

a. a third comparator means for summing the levels of said constant DC signal and said buffered positional information signal, for comparing said sum to a third threshold level, and for allowing said summed signal to continue through said control circuit if said summed signal exceeds said third threshold level; and b. a transistor for allowing activation of said lifting means upon said transistor becoming electrically biased by said summed signal.

19. An orthosis according to claim 1, wherein said muscle activity sensing means includes:

i. a plurality of electrodes attached to the surface of the skin of said leg over said muscles; and ii. a plurality of wires electrically connected at one end to said electrodes and electrically connected at the other end to said control means.

20. A method for rehabilitating a person having a foot-drop disability using a biofeedback-activated orthosis, which comprises the steps of:

a. sensing the electromyographic activity in the dorsiflexor muscles of an affected leg as a person progresses through a gait cycle;

b. sensing the leg position information between the thigh of said leg and the shin of said leg as said person progresses through said gait cycle;

b. transmitting said electromyographic activity signal and said leg position information signal to a control means for comparison with preset threshold levels so that a processed signal may be sent to a lifting means when both said signals simultaneously exceed their respective said threshold levels;

c. activating said lifting means so that said foot is pulled upward throughout the swing phase of said person's gait cycle; and d. allowing said foot to extend away from said leg by causing said lifting means to release said foot upon heel-strike of said person.

* * * * *